United States Patent
Foss et al.

(10) Patent No.: US 10,526,318 B2
(45) Date of Patent: Jan. 7, 2020

(54) ORAL CANNABINOID RECEPTOR MODULATOR FORMULATIONS

(71) Applicant: THE CLEVELAND CLINIC FOUNDATION, Cleveland, OH (US)

(72) Inventors: Joseph Foss, Gates Mills, OH (US); Mohamed Naguib Attala, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 15/862,721

(22) Filed: Jan. 5, 2018

(65) Prior Publication Data
US 2019/0210999 A1 Jul. 11, 2019

(51) Int. Cl.
| | |
|---|---|
| A61P 25/02 | (2006.01) |
| A61K 9/16 | (2006.01) |
| A61K 31/443 | (2006.01) |
| A61P 25/30 | (2006.01) |
| A61P 25/04 | (2006.01) |
| A61K 31/343 | (2006.01) |
| C07D 405/06 | (2006.01) |
| C07D 307/79 | (2006.01) |

(52) U.S. Cl.
CPC .......... *C07D 405/06* (2013.01); *A61K 9/1652* (2013.01); *A61K 31/343* (2013.01); *A61K 31/443* (2013.01); *A61P 25/02* (2018.01); *A61P 25/04* (2018.01); *A61P 25/30* (2018.01); *C07D 307/79* (2013.01)

(58) Field of Classification Search
None
See application file for complete search history.

(56) References Cited

U.S. PATENT DOCUMENTS

| | | | | | |
|---|---|---|---|---|---|
| 4,296,104 | A | * | 10/1981 | Herschler ................ | A61K 8/42 424/679 |
| 5,368,844 | A | * | 11/1994 | Gaffar .................... | A61K 8/347 424/49 |
| 6,475,470 | B1 | * | 11/2002 | Kayane ................... | A46D 1/00 424/49 |
| 8,440,832 | B2 | | 5/2013 | Attala et al. | |
| 2011/0033529 | A1 | * | 2/2011 | Samantaray ......... | A61K 9/4858 424/456 |

FOREIGN PATENT DOCUMENTS

| | | |
|---|---|---|
| WO | 2009/012221 A1 | 1/2009 |
| WO | 2014/011949 A2 | 1/2014 |

OTHER PUBLICATIONS

Naguib et al. "MDA7: A Novel Selective Agonist for CB2 Receptors That Prevents Allodynia in Rat Neuropathic Pain Models". British Journal of Pharmacology. 2008; 155:1104-1116. (Year: 2008).*

Astruc-Diaz et al. "In Vivo Efficacy of Enabling Formulations Based on Hydroxypropyl-Beta-Cyclodextrins, Micellar Preparation, and Liposomes for the Lipophilic Cannabinoid CB2 Agonist, MDA7". Journal of Pharmaceutical Sciences. Feb. 2013; 102(2):352-364. (Year: 2013).*
Friesen et al. "Hydroxypropyl Methylcellulose Acetate Succinate-Based Spray-Dried Dispersions: An Overview". Molecular Pharmaceutics. 2008; 5(6):1003-1019. (Year: 2008).*
Baker, David, et al. "Cannabinoids control spasticity and tremor in a multiple sclerosis model." Nature 404.6773 (2000): 84.
Berghuis, Paul, et al. "Hardwiring the brain: endocannabinoids shape neuronal connectivity." Science 316.5828 (2007): 1212-1216.
Blazquez, Cristina, et al. "Cannabinoid receptors as novel targets for the treatment of melanoma." The FASEB journal 20.14 (2006): 2633-2635.
Crowley, Vivion EF, Giles SH Yeo, and Stephen O'Rahilly. "Obesity therapy: altering the energy intake-and-expenditure balance sheet." Nature reviews Drug discovery 1.4 (2002): 276.
Curatolo, William, James A. Nightingale, and Scott M. Herbig. "Utility of hydroxypropylmethylcellulose acetate succinate (HPMCAS) for initiation and maintenance of drug supersaturation in the GI milieu." Pharmaceutical research 26.6 (2009): 1419-1431.
Di Marzo, Vincenzo, et al. "Leptin-regulated endocannabinoids are involved in maintaining food intake." Nature 410.6830 (2001): 822.
Fride, E. "Endocannabinoids in the central nervous system—an overview." Prostaglandins, Leukotrienes and Essential Fatty Acids (PLEFA) 66.2-3 (2002): 221-233.
Van Gaal, Luc F., et al. "Effects of the cannabinoid-1 receptor blocker rimonabant on weight reduction and cardiovascular risk factors in overweight patients: 1-year experience from the RIO-Europe study." The Lancet 365.9468 (2005): 1389-1397.
Guzman, Manuel. "Cannabinoids: potential anticancer agents." Nature Reviews Cancer 3.10 (2003): 745.
Idris, Aymen I., et al. "Regulation of bone mass, bone loss and osteoclast activity by cannabinoid receptors." Nature medicine 11.7 (2005): 774.
Kalsi, Vinay, and Clare J. Fowler. "Therapy Insight: bladder dysfunction associated with multiple sclerosis." Nature Reviews Urology 2.10 (2005): 492.
Karsak, Meliha, et al. "Attenuation of allergic contact dermatitis through the endocannabinoid system." science 316.5830 (2007): 1494-1497.
Kathuria, Satish, et al. "Modulation of anxiety through blockade of anandamide hydrolysis." Nature medicine 9.1 (2003): 76.
Kehl, Lois J., et al. "A cannabinoid agonist differentially attenuates deep tissue hyperalgesia in animal models of cancer and inflammatory muscle pain." PAIN® 103.1-2 (2003): 175-186.
Maccarrone, Mauro, et al. "The Endocannabinoid System in Human Keratinocytes Evidence That Anandamide Inhibits Epidermal Differentiation Through CB1 Receptor-Dependent Inhibition of Protein Kinase C, Activating Protein-1, and Transglutaminase." Journal of Biological Chemistry 278.36 (2003): 33896-33903.

(Continued)

*Primary Examiner* — Leslie A. Royds Draper
(74) *Attorney, Agent, or Firm* — Tarolli, Sundheim, Covell & Tummino LLP

(57) ABSTRACT

Oral formulations of benzofuran compounds which modulate cannabinoid receptors are presented. Methods of using these formulations for treatment of cannabinoid receptor-mediated disease, including neuropathic pain and addition, are also described.

2 Claims, 5 Drawing Sheets

(56) References Cited

OTHER PUBLICATIONS

Maldonado, Rafael, Olga Valverde, and Fernando Berrendero. "Involvement of the endocannabinoid system in drug addiction." Trends in neurosciences 29.4 (2006): 225-232.

Maresz, Katarzyna, et al. "Direct suppression of CNS autoimmune inflammation via the cannabinoid receptor CB 1 on neurons and CB 2 on autoreactive T cells." Nature medicine 13.4 (2007): 492.

Onaivi, Emmanuel S., et al. "Discovery of the presence and functional expression of cannabinoid CB2 receptors in brain." Annals of the New York Academy of Sciences 1074.1 (2006): 514-536.

Steffens, Sabine, et al. "Low dose oral cannabinoid therapy reduces progression of atherosclerosis in mice." Nature 434.7034 (2005): 782.

Szczesniak, Anna-Maria, et al. "Ocular hypotensive effects of an intratracheally delivered liposomal ?9-tetrahydrocannabinol preparation in rats." Journal of Ocular Pharmacology & Therapeutics 22.3 (2006): 160-167.

Teixeira-Clerc, Fatima, et al. "CB1 cannabinoid receptor antagonism: a new strategy for the treatment of liver fibrosis." Nature medicine 12.6 (2006): 671.

Trang, T., M. Sutak, and K. Jhamandas. "Involvement of cannabinoid (CB1)-receptors in the development and maintenance of opioid tolerance." Neuroscience 146.3 (2007): 1275-1288.

Wang, Haibin, et al. "Aberrant cannabinoid signaling impairs oviductal transport of embryos." Nature medicine 10.10 (2004): 1074.

Wilkinson, Jonathan D., and Elizabeth M. Williamson. "Cannabinoids inhibit human keratinocyte proliferation through a non-CB1/CB2 mechanism and have a potential therapeutic value in the treatment of psoriasis." Journal of dermatological science 45.2 (2007): 87-92.

Abdelbary, A., A. H. Elshafeey, and G. Zidan. "Comparative effects of different cellulosic-based directly compressed orodispersable tablets on oral bioavailability of famotidine." Carbohydrate polymers 77.4 (2009): 799-806.

Diaz, Philippe, et al. "2, 3-Dihydro-1-Benzofuran Derivatives as a Series of Potent Selective Cannabinoid Receptor 2 Agonists: Design, Synthesis, and Binding Mode Prediction through Ligand-Steered Modeling." ChemMedChem: Chemistry Enabling Drug Discovery 4.10 (2009): 1615-1629.

\* cited by examiner

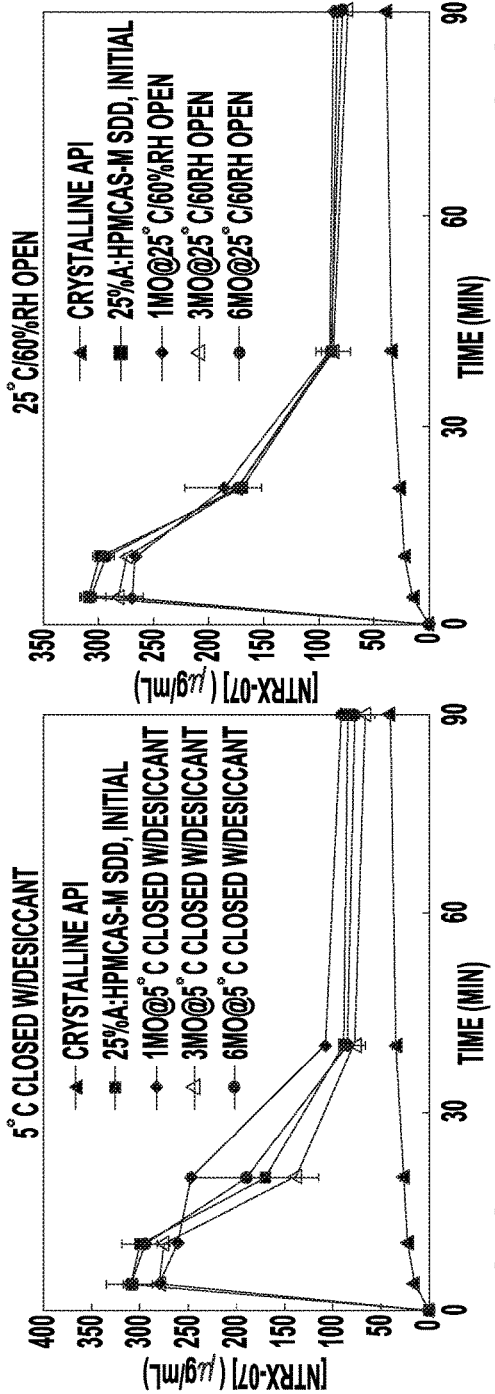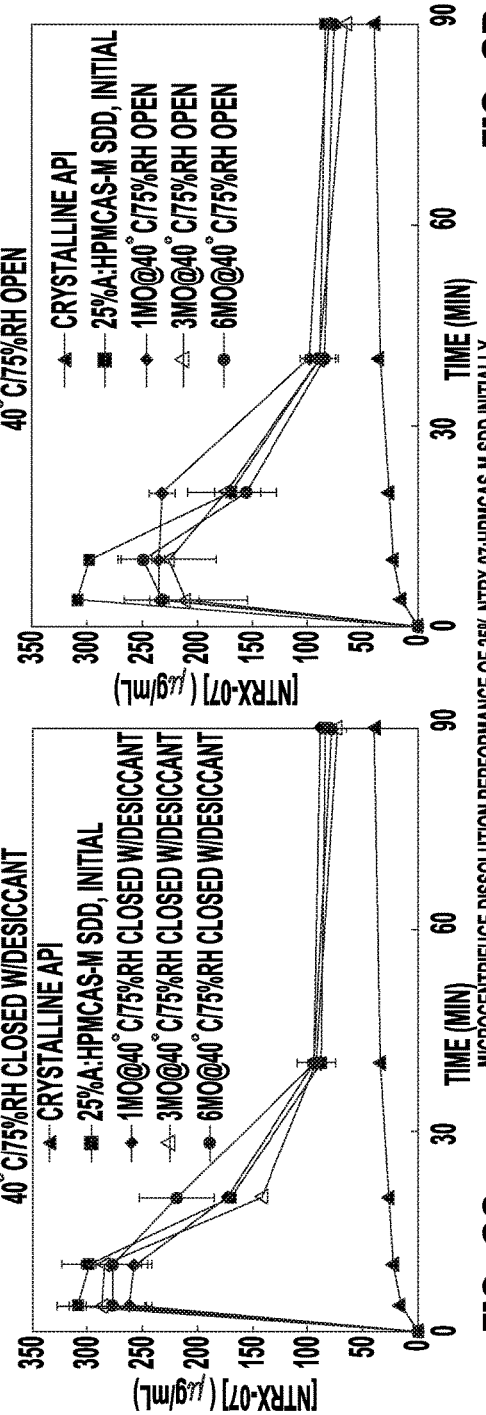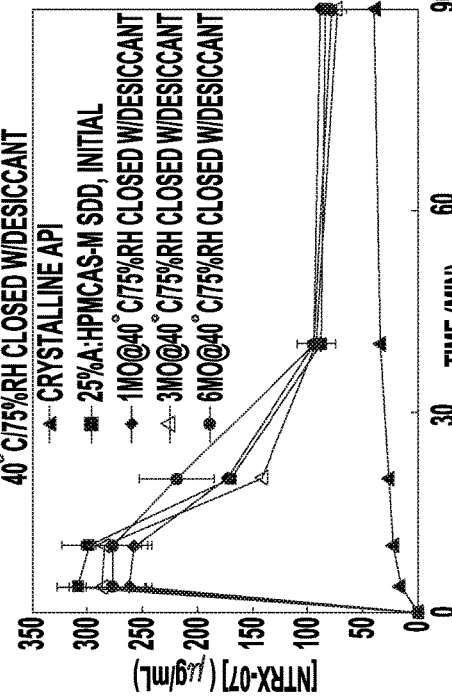

ORAL CANNABINOID RECEPTOR MODULATOR FORMULATIONS

BACKGROUND

CB1 and CB2 are two cannabinoid receptors that belong to the GPCR family and have very different functions and distribution. While no x-ray structure is available for these receptors, various models have been described on the basis of the x-ray structure of rhodopsin, a GPCR belonging protein responsible of the light sensitivity in vision. Matsuda L A, Lolait S J, Brownstein M J, Young A C, Bonner T I, *Structure of a Cannabinoid Receptor and Functional Expression of the Cloned cDNA*, Nature 1990, 346:561-4. CB1 is abundantly expressed in the central nervous system and is most dense in the basal ganglia, cerebellum, hippocampus, and cortex and in the peripheral nervous system, it is expressed in such sites as the testis, eye, urinary bladder, and adipocytes. CB2 is mainly expressed in the immune tissues, in cells such as those in the thymus, marrow, spleen, pancreas, and in glioma and skin tumor cells. It was recently demonstrated that CB2 receptors and their gene transcripts are widely distributed in the brain. A third cannabinoid receptor seems to be present as some chemical analogues exhibit cannabinoid biological activity without activating CB1 and CB2. Di Marzo V, Bifulco M, De Petrocellis L, *The Endocannabinoid System and Its Therapeutic Exploitation*, Nat Rev Drug Discov 2004, 3:771-84.

Solubility is important for any oral solid dosage form of cannabinoid receptor modulating compounds, as the compounds must be released, dissolved in aqueous gastrointestinal media, traverse the endothelial barrier, and bypass various metabolic enzymes to reach systemic circulation and deliver a therapeutic effect. If the cannabinoid receptor modulating compound does not dissolve, it will be wasted, passing through the gastrointestinal tract without serving its intended pharmacological purpose. The development of effective oral dosage forms for poorly soluble compounds such as cannabinoid receptor agonists and antagonists therefore represents a significant challenge.

Bioavailability is a subcategory of absorption and is the fraction of an administered dose of unchanged drug that reaches the systemic circulation, one of the principal pharmacokinetic properties of drugs. By definition, when a medication is administered intravenously, its bioavailability is 100%. However, when a medication is administered via other routes (such as orally), its bioavailability generally decreases, due to incomplete absorption and first-pass metabolism. Many cannabinoid receptor agonists are hydrophobic, and suffer from poor bioavailability when administered orally. Accordingly, there remains a need for improved formulations for oral administration of hydrophobic cannabinoid receptor agonists.

SUMMARY OF THE INVENTION

Novel oral formulations for benzofuran compounds that modulate CB1 and CB2 have been found. These formulations can be used to prepare pharmaceutical compositions having improved oral bioavailability, and using the pharmaceutical compositions in methods of treatment of cannabinoid receptor-mediated diseases.

A class of benzofuran compounds, useful in treating cannabinoid receptor mediated disorders and conditions, is presented and defined by the structural Formula I:

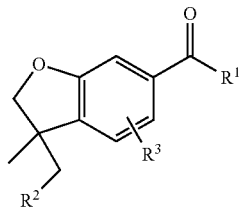

or a salt, ester or prodrug thereof, wherein:
  $R^1$ is selected from the group consisting of $NH_2$, $NHR^4$, $NR^4R^5$, any carbon atom of which may be optionally substituted;
  $R^2$ is selected from the group consisting of hydrogen, aryl, alkyl, cycloalkyl, aralkyl, alkenyl, and alkynyl, any carbon atom of which may be optionally substituted;
  $R^3$ is selected from the group consisting of hydrogen, halogen, alkyl, cycloalkyl, aryl, and heteroaryl, any carbon atom of which may be optionally substituted; and
  $R^4$ and $R^5$ vary independently and are selected from the group consisting of aryl, alkyl, cycloalkyl, aralkyl, alkenyl, and alkynyl, any carbon atom of which may be optionally substituted, and by the structural Formula III:

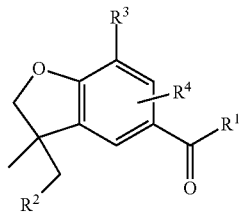

or a salt, ester or prodrug thereof, wherein:
  $R^1$ is selected from the group consisting of $NH_2$, $NHR^5$, $NR^5R^6$, any carbon atom of which may be optionally substituted;
  $R^2$ is selected from the group consisting of hydrogen, aryl, alkyl, cycloalkyl, aralkyl, alkenyl, and alkynyl, any carbon atom of which may be optionally substituted;
  $R^3$ and $R^4$ are independently selected from the group consisting of hydrogen, halogen, alkyl, cycloalkyl, aryl, and heteroaryl;
  $R^5$ and $R^6$ are independently selected from the group consisting of aryl, alkyl, cycloalkyl, aralkyl, alkenyl, and alkynyl; and
  when $R^2$ is hydrogen, $R^3$ is not t-butyl, bromo, methoxy, or

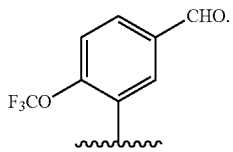

Benzofuran compounds presented herein possess useful cannabinoid receptor modulating activity, and may be used in the treatment or prophylaxis of a disease or condition in which a cannabinoid receptor plays an active role. Thus, in broad aspect, pharmaceutical compositions are provided comprising one or more the compounds together with a pharmaceutically acceptable carrier, as well as methods of making and using the compounds and compositions.

Methods for modulating cannabinoid receptors with pharmaceutical compositions including benzofuran compounds are also provided. Methods for treating a cannabinoid receptor-mediated disorder such as neuropathic pain or addiction in a patient in need of such treatment comprising administering to said patient a therapeutically effective amount of a benzofuran compound in a pharmaceutical composition presented herein. The use of compounds disclosed herein can be used in the manufacture of a medicament for the treatment of a disease or condition ameliorated by the modulation of cannabinoid receptors.

BRIEF DESCRIPTION OF THE FIGURES

The foregoing summary as well as the following detailed description of the preferred embodiment of the invention will be better understood when read in conjunction with the appended drawings. It should be understood, however, that the invention is not limited to the precise arrangements and instrumentalities shown herein.

For a more complete understanding of the present invention, and the advantages thereof, reference is now made to the following descriptions taken in conjunction with the accompanying drawings, in which:

FIGS. 6A-6D provide graphs showing microcentrifuge dissolution performance of 25% NTRX-07:HPMCAS-M SDD initially and after storage for up to 6 months. FIG. 6A shows the results at 5° C. closed with desiccant, FIG. 6B shows the results at 40° C./75% RH closed with desiccant, FIG. 6C shows the results at 25° C./60% RH open, and FIG. 6D shows the results at 40° C./75% RH open.

DETAILED DESCRIPTION OF THE INVENTION

Benzofuran Compounds

Figure 1:
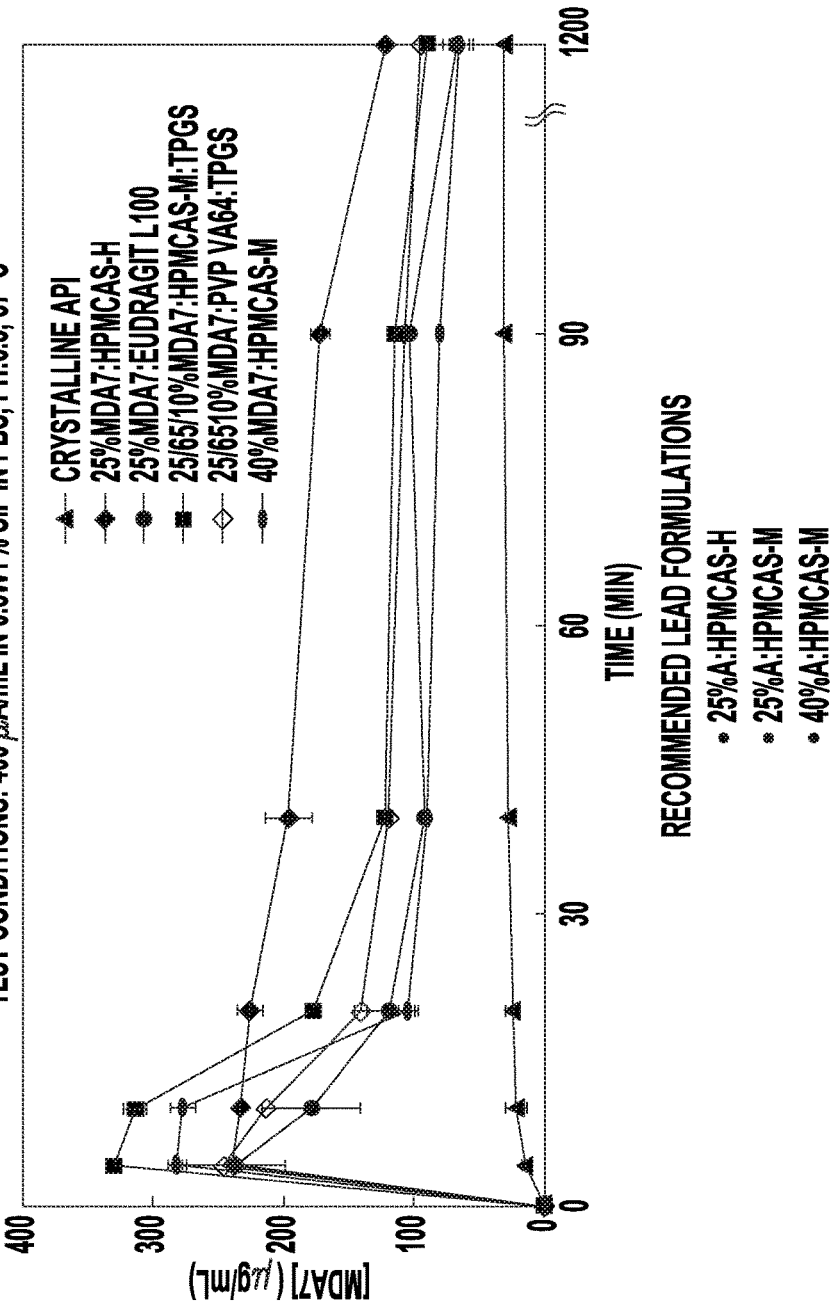
FIG. 1 provides a graph showing MDA7 GB/1B non-sink microcentrifuge dissolution test results.

Benzofuran compounds suitable for use in the pharmaceutical compositions described herein include compounds defined by the structural Formula II:

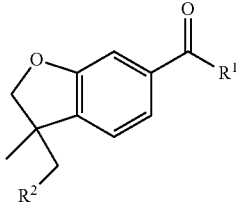

or a salt, ester or prodrug thereof, wherein:
$R^1$ is selected from the group consisting of $NH_2$, $NHR^3$, $NR^3R^4$, any carbon atom of which may be optionally substituted;
$R^2$ is selected from the group consisting of hydrogen, aryl, alkyl, cycloalkyl, aralkyl, alkenyl, and alkynyl, any carbon atom of which may be optionally substituted; and
$R^3$ and $R^4$ are independently selected from the group consisting of aryl, alkyl, cycloalkyl, aralkyl, alkenyl, and alkynyl, any carbon atom of which may be optionally substituted,
and by the structural Formula IV:

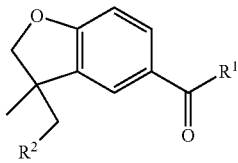

or a salt, ester or prodrug thereof, wherein:
$R^1$ is selected from the group consisting of $NH_2$, $NHR^3$, $NR^3R^4$, any carbon atom of which may be optionally substituted;
$R^2$ is selected from the group consisting of hydrogen, aryl, alkyl, cycloalkyl, aralkyl, alkenyl, and alkynyl, any of carbon atom of which may be optionally substituted;
$R^3$ and $R^4$ are independently selected from the group consisting of aryl, alkyl, cycloalkyl, aralkyl, alkenyl, and alkynyl, any carbon atom of which may be optionally substituted; and
when $R^2$ is hydrogen, $R^1$ is not $NH_2$,

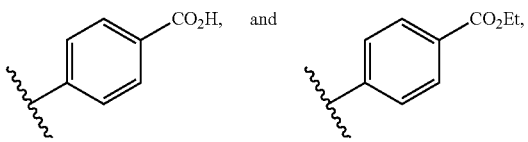 [SMILES: *c1ccc(C(=O)O)cc1 ; *c1ccc(C(=O)OCC)cc1]

and by the structural Formula V:

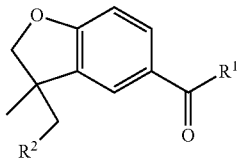

or a salt, ester or prodrug thereof, wherein:
$R^1$ is selected from the group consisting of cyclohexylamino, piperidinyl, and o-iodoanilino; and
$R^2$ is optionally substituted phenyl,
and by the structural Formula VI:

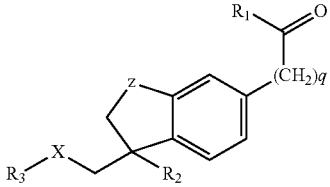

or a salt, ester or prodrug thereof, wherein:
q is an integer ranging from 0 to 2
X is absent or present and represents a —O—, —S—, —Se—, $NR^6$, SO—, —$SO_2$—,
Z represents a —O—, —S—, —SO—, —$SO_2$—, —Se— or NR'
$R^1$ is selected from the group consisting of $NH_2$, $NHR^4$, $NR^4R^5$, aryl, a heteroaryl alkyl, cycloalkyl, aralkyl, alkenyl, and alkynyl, any carbon atom of which may be optionally substituted $R^2$ is selected from the group consisting of hydrogen, alkyl, cycloalkyl, aralkyl, alkenyl, and alkynyl, an alkoxyl, any carbon atom of which may be optionally substituted;

$R^3$ is selected from the group consisting of aryl, a heteroaryl, alkyl, cycloalkyl, aralkyl, alkenyl, and alkynyl, any carbon atom of which may be optionally substituted;

$R^4$ and $R^5$ vary independently and are selected from the group consisting of aryl, alkyl, cycloalkyl, aralkyl, alkenyl, and alkynyl, any carbon atom of which may be optionally substituted, $R^6$ is selected from the group consisting of hydrogen, aryl, alkyl, cycloalkyl, aralkyl, alkenyl, and alkynyl, any carbon atom of which may be optionally substituted, $R^7$ is selected from the group consisting of hydrogen, aryl, alkyl, cycloalkyl, aralkyl, alkenyl, and alkynyl, any carbon atom of which may be optionally substituted.

Novel compounds presented further include compounds defined by the structural Formula VII:

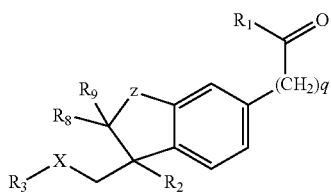

or a salt, ester or prodrug thereof, wherein:

q is an integer ranging from 0 to 2

X is absent or present and represents a —O—, —S—, —Se—, $NR^6$, SO—, —$SO_2$—,

Z represents a —O—, —S—, —SO—, —$SO_2$—, —Se— or NR'

$R^1$ is selected from the group consisting of $NH_2$, $NHR^4$, $NR^4R^5$, aryl, a heteroaryl alkyl, cycloalkyl, aralkyl, alkenyl, and alkynyl, any carbon atom of which may be optionally substituted $R^2$ is selected from the group consisting of hydrogen, alkyl, cycloalkyl, aralkyl, alkenyl, and alkynyl, an alkoxyl, any carbon atom of which may be optionally substituted;

$R^3$ is selected from the group consisting of aryl, a heteroaryl, alkyl, cycloalkyl, aralkyl, alkenyl, and alkynyl, any carbon atom of which may be optionally substituted;

$R^4$ and $R^5$ vary independently and are selected from the group consisting of aryl, alkyl, cycloalkyl, aralkyl, alkenyl, and alkynyl, any carbon atom of which may be optionally substituted, $R^6$ is selected from the group consisting of hydrogen, aryl, alkyl, cycloalkyl, aralkyl, alkenyl, and alkynyl, any carbon atom of which may be optionally substituted, $R^3$ and $R^6$ taken together might form a cycloalkyl containing from 3 to 10 carbon atoms and eventually interrupted with one or more hetero atoms or by —CO—, —SO—, —$SO_2$—, —CHOH— or —$NR^{13}$—;

$R^7$ is selected from the group consisting of hydrogen, aryl, alkyl, cycloalkyl, aralkyl, alkenyl, and alkynyl, any carbon atom of which may be optionally substituted, $R^8$ and $R^9$ are selected from the group consisting of hydrogen, alkyl, an alkoxyl or taken together might form a carbonyl.

Definitions

As used herein, the terms below have the meanings indicated.

The term "acyl," as used herein, alone or in combination, refers to a carbonyl attached to an alkenyl, alkyl, aryl, cycloalkyl, heteroaryl, heterocyclyl, or any other moiety were the atom attached to the carbonyl is carbon. An "acetyl" group refers to a —$C(O)CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20, preferably 2 to 6, carbon atoms. Alkenylene refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—).

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20, preferably from 2 to 6, more preferably from 2 to 4, carbon atoms. "Alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl," as used herein, alone or in combination, means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term "aryloxy," as used herein, alone or in combination, refers to an aryl group attached to the parent molecular moiety through an oxy.

According to the present invention, the expression alkyl radicals understood to mean a linear optionally branched and optionally fluorinated radical. In certain embodiments, alkyl radicals having from 6 to 12 carbon atoms are 2-Methylpentan-2-yl, 3,3-Dimethyl-butan-1-yl, hexyl, heptyl, octyl, nonyl, decyl, dodecyl. "Alkyl radicals" containing from 1 to 3 carbon atoms, are linear or branched radicals containing, respectively, from 1 to 3. Preferably, the alkyl radicals containing from 1 to 3 carbon atoms are methyl, ethyl, n-propyl, or 2-propyl radicals. The expression "alkoxyl radical" is understood to mean a radical containing from 1 to 3 carbon atoms, such as methoxyl, ethoxyl, propyloxyl or isopropyloxyl radicals.

The term "aryl radical" means a phenyl or a naphthyl radical, eventually mono- or disubstituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 12 carbon atoms.

The term "heteroaryl" means an aryl radical interrupted with one or more hetero atoms, such as a thiophenyl, thiazolyl or imidazolyl radical, optionally substituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 6 carbon atoms.

The term "polyether radical" means a polyether radical containing from 2 to 6 carbon atoms interrupted with at least one oxygen atom, such as methoxymethoxy, ethoxymethoxy or methoxyethoxymethoxy radicals.

The term "halogen atom" includes, but is not limited to, fluorine, chlorine or bromine atom.

The terms "benzo" and "benz," as used herein, alone or in combination, refer to the divalent radical C$_6$H$_4$= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydonapthalene, octahydronapthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to 3 to 7 membered, preferably 5 to 7 membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groupsinclude carbazolyl, benzidolyl, phenanthrolinyl, dibenzofuranyl, acridinyl, phenanthridinyl, xanthenyl and the like.

The terms "heterocycloalkyl" and, interchangeably, "heterocyclyl," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocyclyl" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocyclyl groups are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocyclyl groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of this invention.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in combination, means containing from 1 to and including 6 carbon atoms.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocyclyl, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Optical isomers are compounds with the same molecular formula but differ in the way they rotate plane polarized light. There are two kinds of optical isomers. The first optical isomer are compounds that are mirror images of one another but cannot be superimposed on each other. These isomers are called "enantiomers". The second optical isomers are molecules that are not mirror images but each molecule rotates plane polarized light and are considered optically active. Such molecules are called "diastereoisomers". Diasteroisomers differ not only in the way they rotate plane polarized light, but also their physical properties. The term "optical isomer" comprises more particularly the enantiomers and the diastereoisomers, in pure form or in the form of a mixture.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"Cannabinoid receptor modulator" is used herein to refer to a compound that exhibits an $EC_{50}$ or $IC_{50}$ with respect to a cannabinoid receptor activity of no more than about 100 µM and more typically not more than about 50 µM, as measured in the cannabinoid receptor assay described generally herein below. "$EC_{50}$" is that concentration of modulator which activates the activity of a cannabinoid receptor to half-maximal level. "$IC_{50}$" is that concentration of modulator which reduces the activity of a cannabinoid receptor to half-maximal level. This test will be done during the exemplification period.

The term "modulator" described herein reflects any chemical compound that will act as full agonist, partial agonist, inverse agonist or as an antagonist at any known or yet to be discovered/identified cannabinoid receptor.

Compounds described herein have been discovered to exhibit modulatory activity against cannabinoid receptors and exhibit an $EC_{50}$ or $IC_{50}$ with respect to a cannabinoid receptor of no more than about 10 µM, more preferably, no more than about 5 µM, even more preferably not more than about 1 µM, and most preferably, not more than about 200 nM, as measured in the assays described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds of the present invention may also exist as prodrugs, as described in *Hydro-lysis in Drug and Prodrug Metabolism: Chemistry, Biochemistry, and Enzymology*, Testa, Bernard and Wiley-VHCA, Zurich, Switzerland 2003. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. Prodrugs are often useful because, in some situations, they may be easier to administer than the compound, or parent drug. They may, for instance, be bio-available by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

"Pharmaceutically acceptable carrier" refers herein to a composition suitable for delivering an active pharmaceutical ingredient, such as the composition of the present invention, to a subject without excessive toxicity or other complications while maintaining the biological activity of the active pharmaceutical ingredient. Protein-stabilizing excipients, such as mannitol, sucrose, glucose, polysorbate-80 and phosphate buffers, polymers such as polyethylene glycol (PEG), polyvinyl alcohol (PVA), pluronics, are typically found in such carriers, although the carriers should not be construed as being limited only to these compounds.

"Biocompatible," as used herein, refers to any material that does not cause injury or death to the animal or induce an adverse reaction in an animal when placed in intimate contact with the animal's tissues. Adverse reactions include for example inflammation, infection, fibrotic tissue formation, cell death, or thrombosis. The terms "biocompatible" and "biocompatibility" when used herein are art-recognized and mean that the referent is neither itself toxic to a host (e.g., an animal or human), nor degrades (if it degrades) at a rate that produces byproducts (e.g., monomeric or oligomeric subunits or other byproducts) at toxic concentrations, does not cause prolonged inflammation or irritation, or does not induce more than a basal immune reaction in the host. It is not necessary that any subject composition have a purity of 100% to be deemed biocompatible. Hence, a subject composition may comprise 99%, 98%, 97%, 96%, 95%, 90% 85%, 80%, 75% or even less of biocompatible agents, e.g., including polymers and other materials and excipients described herein, and still be biocompatible.

The term "biodegradable" as used herein refers to a polymer that can be broken down by either chemical or physical process, upon interaction with the physiological environment subsequent to administration, and erodes or dissolves within a period of time, typically within days, weeks or months. A biodegradable material serves a temporary function in the body, and is then degraded or broken into components that are metabolizable or excretable.

The compounds of the present invention can exist as therapeutically acceptable salts. The present invention includes compounds listed above in the form of salts, in particular acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Stahl, P. Heinrich, *Pharmaceutical Salts: Properties, Selection, and Use*, Wiley-VCHA, Zurich, Switzerland, 2002.

The term "therapeutically acceptable salt," as used herein, represents salts or zwitterionic forms of the compounds of the present invention which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

Basic addition salts can be prepared during the final isolation and purification of the compounds by reaction of a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid. The novel compounds described in this patent could be prepared in a form of pharmaceutically acceptable salts that will be prepared from nontoxic inorganic or organic bases including but not limited to aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, ethylamine, 2-diethylaminoethano, 1,2-dimethylaminoethanol, ethanolarnine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, trishydroxylmethyl amino methane, tripropyl amine, and tromethamine.

If the novel compounds described in this patent are basic, salts could be prepared in a form of pharmaceutically acceptable salts that will be prepared from nontoxic inorganic or organic acids including but not limited to hydrochloric, hydrobromic, phosphoric, sulfuric, tartaric, citric, acetic, fumaric, alkylsulphonic, naphthalenesulphonic, paratoluenesulphonic, camphoric acids, benzenesulfonic, benzoic, camphorsulfonic, citric, ethanesulfonic, gluconic, glutamic, isethonic, lactic, maleic, malic, mandelic, methanesulfonic, mucic, nitric, pamoic, pantothenic, phosphoric, and succinic.

Formulation and Administration

While it may be possible for the compounds of the subject invention to be administered as the raw chemical, it is also possible to present them as a pharmaceutical formulation including a pharmaceutically acceptable carrier. Accordingly, the subject invention provides a pharmaceutical formulation comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. Embodiments in which the pharmaceutically acceptable carrier is suitable for oral administration are preferred. The formulations may conveniently be presented in unit dosage form and may be prepared by any of the methods well known in the art of pharmacy. All methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

In some embodiments, the pharmaceutically acceptable carrier is a polymer. Examples of polymers suitable for oral administration of benzofuran compounds include biocompatible and biodegradable polymers.

Examples of biocompatible polymers include natural or synthetic polymers such as polystyrene, polylactic acid, polyketal, butadiene styrene, styreneacrylic-vinyl terpolymer, polymethylmethacrylate, polyethylmethacrylate, poly-alkylcyanoacrylate, styrene-maleic anhydride copolymer, polyvinyl acetate, polyvinylpyridine, polydivinylbenzene, polybutyleneterephthalate, acrylonitrile, vinylchloride-acrylates, polycaprolactone, poly(alkyl cyanoacrylates), poly(lactic-co-glycolic acid), and the like.

In further embodiments, the pharmaceutically acceptable carrier comprises one or more biodegradable polymers. Use of biodegradable polymers provides the advantages of using a formulation that will eventually disintegrate, which facilitates release of the benzofuran compound and elimination of the carrier in vivo. However, benzofuran compounds can also be released from the matrix of non-biodegradable polymers as a result of gradual efflux from channels within the polymer matrix, including those formed by soluble materials included in the polymer matrix.

Examples of biodegradable polymers include polylactide polymers include poly(D,L-lactide)s; poly(lactide-co-glycolide) (PLGA) copolymers; polyglycolide (PGA) and polydioxanone; caprolactone polymers; chitosan; hydroxybutyric acids; polyanhydrides and polyesters; polyphosphazenes; and polyphosphoesters. A preferred biodegradable polymer for use in the nanoparticles is poly-(DL-lactide-co-glycolide).

Functionalized poly(D,L-lactide)s can also be used as biodegradable polymers in the nanoparticles of the invention. Examples of functionalized poly(D,L-lactide)s include poly(L-lactide), acrylate terminated; poly(L-lactide), amine terminated; poly(L-lactide), azide terminated; poly(L-lactide), 2-bromoisobutyryl terminated; poly(L-lactide), 2-bromoisobutyryl terminated; poly(L-lactide) 4-cyano-4-[(dodecylsulfanylthiocarbonyl)sulfanyl]pentonate; poly(L-lactide) N-2-hydroxyethylmaleimide terminated; poly(L-lactide) 2-hydroxyethyl, methacrylate terminated; poly(L-lactide), propargyl terminated; poly(L-lactide), thiol terminated;

Other biodegradable polymers that can be used in the nanoparticles include AB diblock copolymers such as poly(ethylene glycol) methyl ether-block-poly(D,L-lactide); poly(ethylene glycol) methyl ether-block-poly(lactide-co-glycolide) PEG; poly(ethylene glycol)-block-poly(ε-caprolactone) methyl ether PEG; and polypyrrole-block-poly(caprolactone). Further biodegradable polymers include ABA triblock copolymers such as polylactide-block-poly(ethylene glycol)-block-polylactide PLA; poly(lactide-co-glycolide)-block-poly(ethylene glycol)-block-poly(lactide-co-glycolide); poly(lactide-co-caprolactone)-block-poly(ethylene glycol)-block-poly(lactide-co-caprolactone); polycaprolactone-block-polytetrahydrofuran-block-poly-caprolactone; and polyglycolide-block-poly(ethylene glycol)-block-polyglycolide PEG.

Biodegradable polymers also include various natural polymers. Examples of natural polymers include polypeptides including those modified non-peptide components, such as saccharide chains and lipids; nucleotides; sugar-based biopolymers such as polysaccharides; cellulose; carbohydrates and starches; dextrans; lignins; polyamino acids; adhesion proteins; lipids and phospholipids (e.g., phosphorylcholine).

In some embodiments, the polymer is a cellulose derivative such as hydroxypropyl methylcellulose polymers. Hydroxypropyl methyl cellulose (HPMC) is a non-ionic cellulose ether made through a series of chemical processes, with the natural polymer cellulose as the raw material. The product is a non-ionic cellulose ether in the shape of white powder, odorless and tasteless. HPMC is also known as hypromellose, is a methylcellulose modified with a small amount of propylene glycol ether groups attached to the anhydroglucose of the cellulose.

In some embodiments, the polymer is a functionalized HPMC polymer. For example, the polymer can be hydroxypropyl methylcellulose acetate succinate (HPMCAS). HPMCAS is functionalized with a mixture of monosuccinic acid and acetic acid esters, and is also known as AFFINISOL™. HPMCAS is available in various different grades (e.g., HPMCAS-H and HPMCAS-M) differentiated by the ratio of succinyl and acetyl substituents on the HPMC backbone. HPMCAS is soluble in a wide range of organic solvents, making it compatible with a range of different active pharmaceutical ingredients.

In some embodiments, the polymer is a spray-dried polymer dispersion (SDD). Spray-dried dispersions are produced by dissolving the cannabinoid receptor modulator and a polymer (e.g., a cellulose derivative) in an organic solvent or co-solvent mixture, then atomizing the solution in to fine droplets in a drying chamber. The drying medium—typically heated nitrogen gas—evaporates the solvent, leaving the dry amorphous solid dispersion to be collected. Due to rapid solvent evaporation, spray-dried dispersions achieve a thorough mixing of the cannabinoid receptor modulator and the polymer carrier. The SDDs are also flowable and compressible, allowing them to be compressed, for example, into tablets for oral administration.

HPMCAS have been demonstrated to be particularly effective in forming amorphous solid dispersions with poorly soluble active pharmaceutical ingredients such as cannabinoid receptor modulators that result in solubility enhancement through the ability to achieve and sustain a supersaturated solution of the active pharmaceutical ingredient. Curatolo et al., Pharmaceutical Research, 26(6), p. 1419-1431 (2009). The extend of the solubility enhancement and the sustainment is dependent on the acetate and succinate content of the polymer, and varies depending on the specific cannabinoid receptor modulator being administered.

It should be understood that in addition to the ingredients particularly mentioned above, the formulations of this invention may include other agents conventional in the art having regard to the type of formulation in question, for example those suitable for oral administration may include flavoring agents.

Preferred unit dosage formulations are those containing an effective dose, as herein below recited, or an appropriate fraction thereof, of the active ingredient. The amount of active ingredient that may be combined with the carrier materials to produce a single dosage form will vary depending upon the host treated and the particular mode of administration. The compounds of the invention may be administered at a dose of from 0.1 to 500 mg/kg per day. The dose range for adult humans is generally from 5 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

Certain compounds according to the invention can be administered at a daily dose of about 0.001 mg/kg to 100 mg/kg of body weight, in 1 to 3 dosage intakes. Further, certain compounds can be used systemically, at a concentration generally of between 0.001% and 10% by weight and preferably between 0.01% and 1% by weight, relative to the weight of the composition.

The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Treating Cannabinoid Receptor-Mediated Disorders

Methods of treatment of certain diseases and indications in a human or animal subject in need of such treatment are provided herein. Benzofuran compounds described herein can be used alone or in combination with other agents and compounds in the treatment of neuropathic pain, addiction (including nicotine, cocaine, opioids, hashish, marijuana, alcohol dependence, food), cancer (including melanoma, lymphomas, and gliomas), inflammation including autoimmune inflammation, cardiovascular disease, liver fibrosis, obesity, osteoporosis and other bone disease. Additional indications for use of the compounds disclosed herein include acne, psoriasis, allergic contact dermatitis, anxiety, spasticity and tremor, bladder dysfunctions, prevention of miscarriage and ectopic pregnancy, Tourette's, Parkinson's disease, stroke, glaucoma and other diseases of the eye including intraocular pressure, diarrhea and nausea. Each such treatment described above includes the step of administering to a subject in need thereof a therapeutic effective amount of the benzofuran compound described herein to reduce or prevent such disease or indication.

Besides being useful for human treatment, the compounds and formulations of the present invention are also useful for veterinary treatment of companion animals, exotic animals and farm animals, including mammals, rodents, and the like. More preferred animals include horses, dogs, and cats. These benzofuran compounds are also helpful in neuronal growth and development.

Therefore, the compounds described herein may be used alone or in combination with another agent or compound in methods for treating, ameliorating or preventing a syndrome, disorder or disease in which cannabinoid receptor is involved, including, but not limited to, ocular complaint such as glaucoma, pain, controlling appetite, regulating metabolism, diabetes, social and mood disorders, seizure-related disorders, substance abuse disorders, learning, cognition and/or memory disorders, bowel disorders, gastrointestinal disorders, respiratory disorders, locomotor activity disorders, movement disorders, immune disorders or inflammation disorders, and controlling organ contraction and muscle spasm.

The compounds presented herein may be also useful in enhancing learning, cognition and/or memory, regulating cell growth, providing neuroprotection and the like. The compounds presented herein may also be used for treating dermatological complaints associated with a keratinization disorder relating to cell differentiation and proliferation, especially for treating acne, for treating other dermatological complaints with or without cell proliferation disorder, and especially all forms of psoriasis, for treating all dermal or epidermal proliferations, for preventing or treating cicatrization disorders, in the treatment of dermatological or general complaints with an immunological component, in the treatment of skin disorders caused by exposure to UV radiation, and also for combating sebaceous function disorders, for repairing or combating ageing of the skin, for preventing or treating cicatrization disorders, in the treatment of pigmentation disorders.

Historically, cannabinoid preparations have been used for medicinal and recreational purposes for many centuries. Cannabinoids are present in the hemp Cannabis sativa L. Identification of the main active ingredient, tetrahydrocannabinol (Δ9-THC) has been done in 1964. Gaoni Y, Mechoulam R, *Isolation, Structure, and Partial Synthesis of an Active Constituent of Hashish*, J Am Chem Soc 1964, 86:1646-7. The endocannabinoid system was elucidated in the early 1990's. Currently, two receptors belonging to the GPCR family CB1 and CB2, five endogenous lipid ligands and the enzymes involved in their syntheses and metabolism have been identified. Matsuda L A, Lolait S J, Brownstein M J, Young A C, Bonner T I, *Structure Of A Cannabinoid Receptor And Functional Expression Of The Cloned Cdna*, Nature 1990, 346:561-4.

CB1 is abundantly expressed in the central nervous system with highest density level in the basal ganglia, cerebellum, hippocampus and cortex as well as in the peripheral nervous system such as testis, eye, urinary bladder and adipocyte. CB2 is mainly expressed in the immune tissues and cells such as the thymus, marrow, spleen, pancreas and in glioma and skin tumor cells.

CB2 receptors and their gene transcripts have been recently demonstrated as widely distributed in the brain. The multifocal expression of CB2 immunoreactivity in brain suggests that CB2 receptors play a role in the brain and may be involved in depression and substance abuse. See e.g., Onaivi E S, Ishiguro H, Gong J-P, Patel S, Perchuk A, Meozzi P A, Myers L, Mora Z, Tagliaferro P, Gardner E, Brusco A, Akinshola B E, Liu Q-R, Hope B, Iwasaki S, Arinami T, Teasenfitz L, Uhl G R, *Discovery of the Presence and Functional Expression of Cannabinoid CB2 Receptors in Brain*, Ann NY Acad Sci 2006, 1074:514-536; Berghuis P, Rajnicek A M, Morozov Y M, Ross R A, Mulder J, Urban G M, Monory K, Marsicano G, Matteoli M, Canty A, Irving A J, Katona I, Yanagawa Y, Rakic P, Lutz B, Mackie K, Harkany T, *Hardwiring the Brain: Endocannabinoids Shape Neuronal Connectivity*, Science 2007, 316:1212-1216; Kalsi V, Fowler C J, *Therapy Insight: Bladder Dysfunction Associated With Multiple Sclerosis*, Nat Clin Pract Urol 2005, 2:492-501; Kathuria S, Gaetani S, Fegley D, Valino F, Duranti A, Tontini A, Mor M, Tarzia G, Rana G L, Calignano A, Giustino A, Tattoli M, Palmery M, Cuomo V, Piomelli D, *Modulation of Anxiety Through Blockade of Anandamide Hydrolysis*, Nat Med 2003, 9: 76-81; Baker D, Pryce G, Croxford J L, Brown P, Pertwee R G, Huffman J W, Layward L, *Cannabinoids Control Spasticity and Tremor in a Multiple Sclerosis Model*, Nature 2000, 404:84-87. Furthermore, the endocannabinoid system has been implicated in allergic contact dermatitis. Karsak M, Gaffal E, Date R, Wang-Eckhardt L, Rehnelt J, Petrosino S, Starowicz K, Steuder R, Schlicker E, Cravatt B, Mechoulam R, Buettner R, Werner S, Di Marzo V, Tuting T, Zimmer A, *Attenuation of Allergic Contact Dermatitis Through the Endocannabinoid System*, Science 2007, 316:1494-7.

In addition, studies provide support for the role of cannabinoid system in several physiological functions including food consumption and body weight, in which CB1 receptor activation leads to increased food consumption and weight gain. Fride, E., *Endocannabinoids in the Central Nervous System—an Overview*, Prostaglandins Leukot Essent Fatty Acids 2002, 66:221-33. Subsequently, CB1 receptor blockade reduces food consumption and leads to weight loss. Van Gaal L F, Rissanen A M, Scheen A J, Ziegler O, Rossner S, *Effects Of The Cannabinoid-1 Receptor Blocker Rimonabant On Weight Reduction And Cardiovascular Risk Factors In Overweight Patients: 1-Year Experience From The RIO-Europe Study*, The Lancet 2005, 365:1389-1397.

Modulators of CB1/CB2 receptors have been used in different clinical or preclinical studies. Steffens S, Veillard N R, Arnaud C, Pelli G, Burger F, Staub C, Zimmer A, Frossard J-L, Mach F, *Low Dose Oral Cannabinoid Therapy Reduces Progression of Atherosclerosis in Mice*, Nature 2005, 434:782-786. For example, CB1 agonists have been used for treatment of nausea, Tourette's, Parkinson's disease, glaucoma, cancer, diarrhoea, and stroke. Guzman M, *Cannabinoids: Potential Anticancer Agents*, Nature Reviews Cancer 2003, 3:745-755. Further, CB2 agonists have been used for treatment pain, gliomas, lymphomas, and inflammation. Maresz K, Pryce G, Ponomarev E D, Marsicano G, Croxford J L, Shriver L P, Ledent C, Cheng X, Carrier E J, Mann M K, Giovannoni G, Pertwee R G, Yamamura T, Buckley N E, Hillard C J, Lutz B, Baker D, Dittel B N, *Direct Suppression of CNS Autoimmune Inflammation Via the Cannabinoid Receptor CB1 on Neurons and CB2 on Autoreactive T Cells*, Nat Med 2007, 13: 492-497.

Moreover, CB1 antagonists have been used for treatment obesity and addiction. Crowley V E F, Yeo G S H, O'Rahilly S, *Obesity Therapy: Altering the Energy Intake-and-Expenditure Balance Sheet*, Nature Reviews Drug Discovery 2002, 1:276-286; Trang T, Sutak M, Jhamandas K, *Involvement of Cannabinoid (CB1)-Receptors in the Development and Maintenance of Opioid Tolerance*, Neuroscience 2007, 146:1275-1288; Teixeira-Clerc F, Julien B, Grenard P, Van Nhieu J T, Deveaux V, Li L, Serriere-Lanneau V, Ledent C, Mallat A, Lotersztajn S, CB1 *Cannabinoid Receptor Antagonism: A New Strategy For the Treatment of Liver Fibrosis*, Nat Med 2006, 12:671-676. For example, the CB1 antagonist SR141716A reduces food intake in mice. Di Marzo V, Goparaju S K, Wang L, Liu J, Batkai S, Jarai Z, Fezza F, Miura G I, Palmiter R D, Sugiura T, Kunos G, *Leptin-Regulated Endocannabinoids Are Involved In Maintaining Food Intake*, Nature 2001, 410:822-5. Also, CB1 cannabinoid antagonists have been cited to treat drug addiction. Maldonado R, Valverde O, Berrendero F, *Involvement Of The Endocannabinoid System In Drug Addiction*, Trends Neurosci 2006, 29:225-32. Cannabinoids attenuate deep tissue hyperalgesia produced by both cancer and inflammatory conditions. Kehl L J, Hamamoto D T, Wacnik P W, Croft D L, Norsted B D, Wilcox G L, Simone D A, *A Cannabinoid Agonist Differentially Attenuates Deep Tissue Hyperalgesia In Animal Models Of Cancer And Inflammatory Muscle Pain*, Pain 2003, 103:175-86. Cannabinoids also have a good potential for the treatment osteoporosis and other bone diseases. Idris A I, van't Hof R J, Greig I R, Ridge S A, Baker D, Ross R A, Ralston S H, *Regulation Of Bone Mass, Bone Loss And Osteoclast Activity By Cannabinoid Receptors*, Nat Med 2005, 11:774-9. Cannabinoids are able to reduce intraocular pressure. Szczesniak A M, Kelly M E, Whynot S, Shek P N, Hung O. *Ocular hypotensive effects of an intratracheally delivered liposomal delta9-tetrahydrocannabinol preparation in rats*, J Ocul Pharmacol Ther. 2006 June; 22(3):160-7. CB1 has also been shown to be involved in ectopic pregnancy in mice. Wang H, Guo Y, Wang D, Kingsley P J, Marnett L J, Das S K, DuBois R N, Dey S K, *Aberrant Cannabinoid Signaling Impairs Oviductal Transport of Embryos*, Nat Med 2004, 10:1074-1080.

Certain published data demonstrate that human keratinocytes partake in the peripheral endocannabinoid system. CB1 receptors have been implicated in epidermal differentiation and skin development. Maccarrone M, Di Rienzo M, Battista N, Gasperi V, Guerrieri P, Rossi A, Finazzi-Agro A, *The Endocannabinoid System In Human Keratinocytes. Evidence That Anandamide Inhibits Epidermal Differentiation Through CB1 Receptor-Dependent Inhibition Of Protein Kinase C, Activation Protein-1, And Transglutaminase*, J Biol Chem 2003, 278:33896-903. Hence, cannabinoid modulator can be useful in the treatment of skin diseases.

Recently it has been shown that show that cannabinoids inhibit keratinocyte proliferation, and therefore support a potential role for cannabinoids in the treatment of psoriasis. Wilkinson J D, Williamson E M, *Cannabinoids Inhibit Human Keratinocyte Proliferation Through A Non-CB1/CB2 Mechanism And Have A Potential Therapeutic Value In The Treatment Of Psoriasis*, J Dermatol Sci 2007, 45:87-92. Cannabinoid receptors have also been described as novel targets for the treatment of melanoma. Blazquez C, Carracedo A, Barrado L, Real P J, Fernandez-Luna J L, Velasco G, Malumbres M, Guzman M, *Cannabinoid Receptors As Novel Targets For The Treatment Of Melanoma*, Faseb J 2006, 20:2633-5.

Combination Therapy

In certain instances, it may be appropriate to administer at least one of the benzofuran compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for pain involving administration of one of the compounds described herein, increased therapeutic benefit may result by also providing the patient with another therapeutic agent for pain. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of the compounds of the invention together with inert or active compounds, or other drugs including wetting agents, flavor enhancers, preserving agents, stabilizers, humidity regulators, pH regulators, osmotic pressure modifiers, emulsifiers, UV-A and UV-B screening agents, antioxidants, depigmenting agents such as hydroquinone or kojic acid, emollients, moisturizers, for instance glycerol, PEG 400, or urea, antiseborrhoeic or antiacne agents, such as benzoyl peroxide, antibiotics, for instance erythromycin and tetracyclines, antifungal agents such as ketoconazole, agents for promoting regrowth of the hair, for instance Minoxidil (2,4-diamino-6-piperidinopyrimidine 3-oxide), non-steroidal anti-inflammatory agents, carotenoids, and especially p-carotene, antipsoriatic agents such as anthralin and its derivatives, retinoids, i.e. RAR or RXR receptor ligands, corticosteroids or estrogens, alpha-hydroxy acids and α-keto acids or derivatives thereof, such as lactic acid, malic acid, citric acid, and also the salts, amides or esters thereof, or p-hydroxy acids or derivatives thereof, such as salicylic acid and the salts, amides or esters thereof, ion-channel blockers such as potassium-channel blockers, or alternatively, more particularly for the pharmaceutical compositions, in combination with medicaments known to interfere with the immune system, anticonvulsant agents include, and are not limited to, topiramate, analogs of topiramate, carbamazepine, valproic acid, lamotrigine, gabapentin, phenytoin and the like and mixtures or pharmaceutically acceptable salts thereof. Needless to say, a person skilled in the art will take care to select the other compound(s) to be added to these compositions such that the advantageous properties intrinsically associated with the heterocyclic compound are not, or are not substantially, adversely affected by the envisaged addition.

In any case, the multiple therapeutic agents (at least one of which is a compound of the present invention) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, methods for treating cannabinoid receptor-mediated disorders in a human or animal subject in need of such treatment are presented herein, the methods comprising the step of administering to a subject in need thereof an amount of a benzofuran compound effective to reduce or prevent a disorder in combination with at least one additional agent for the treatment of said disorder that is known in the art.

In a related aspect, therapeutic compositions having at least one novel benzofuran compound described herein can be administered in combination with one or more additional agents for the treatment of cannabinoid-mediated disorders.

General Synthetic Methods for Preparing Compounds

The following schemes can be used to practice the present invention.

General synthetic scheme for compounds of Formula I, Formula II, Formula III, Formula IV and Formula V:

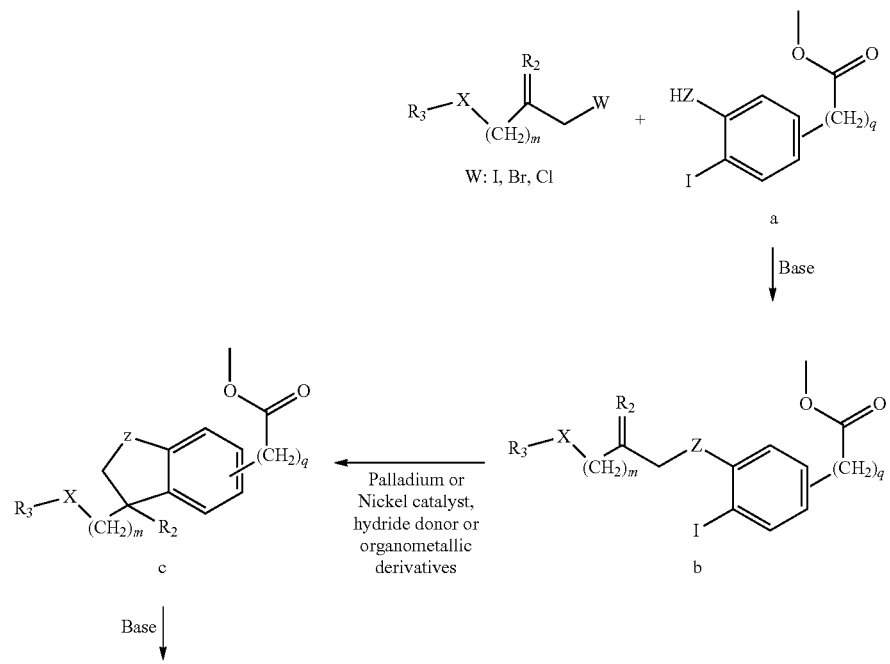

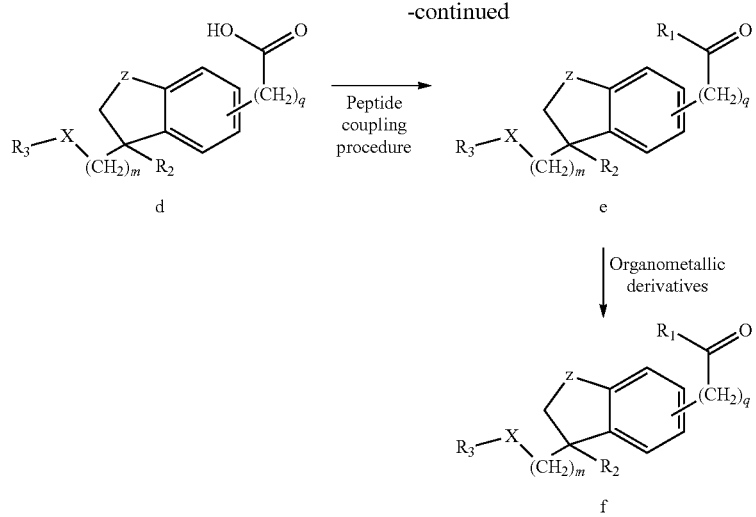

The compounds of Formula I, Formula II, Formula III, Formula IV and Formula V may be obtained by alkylation of the corresponding iodophenol a (Z=O, iodoaniline, Z=N, may be used for indole analogues) using a base such as cesium carbonate or sodium hydride, for example, to provide the phenolic ether b. The phenolic ether is subjected to a transition metal (such as nickel or palladium) catalyzed cyclization in the presence of a hydride donor such as ammonium formate or an organometallic derivatives in order to obtain the cyclized 2,3-dihydrobenzofuran (or indole) product c. After saponification of the ester to yield to the corresponding carboxylic acid d, a peptide coupling procedure using, for example, HATU, DIEA affords the corresponding amide derivatives e (R$_1$=NHR). Using the Weinreb amide (R$_1$=NHOMe) allows for organometallic additions, such as hexyl lithium for example, affording ketone products f in which R$_1$ is, for example, an alkyl or aryl group.

For more detailed information regarding the synthesis of benzofuran compounds described herein, see U.S. Pat. No. 8,440,832, the disclosure of which is incorporated herein by reference. Examples of benzofuran compounds include the compounds shown below:

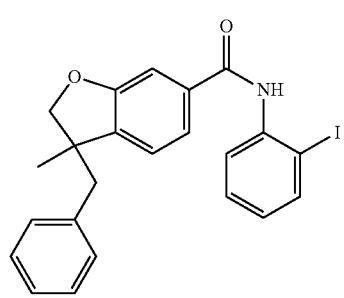

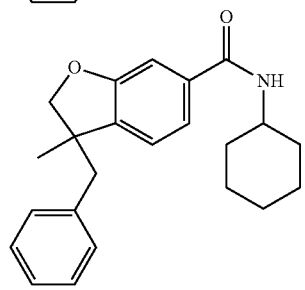

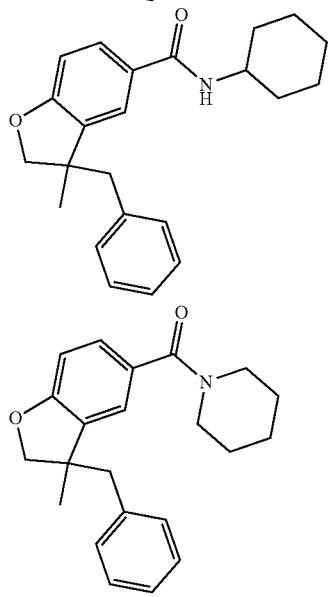

-continued

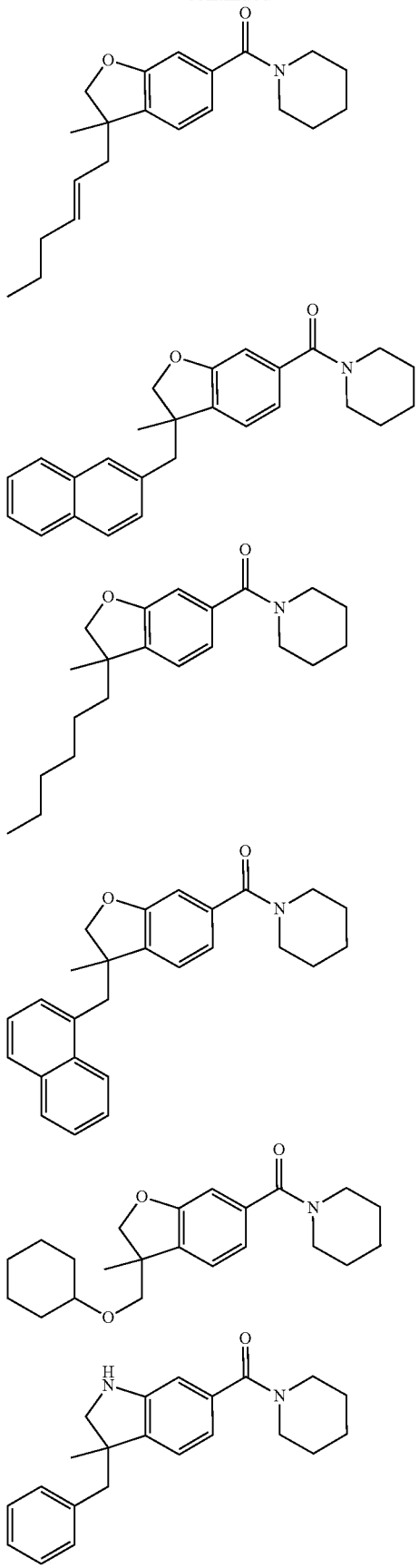

-continued

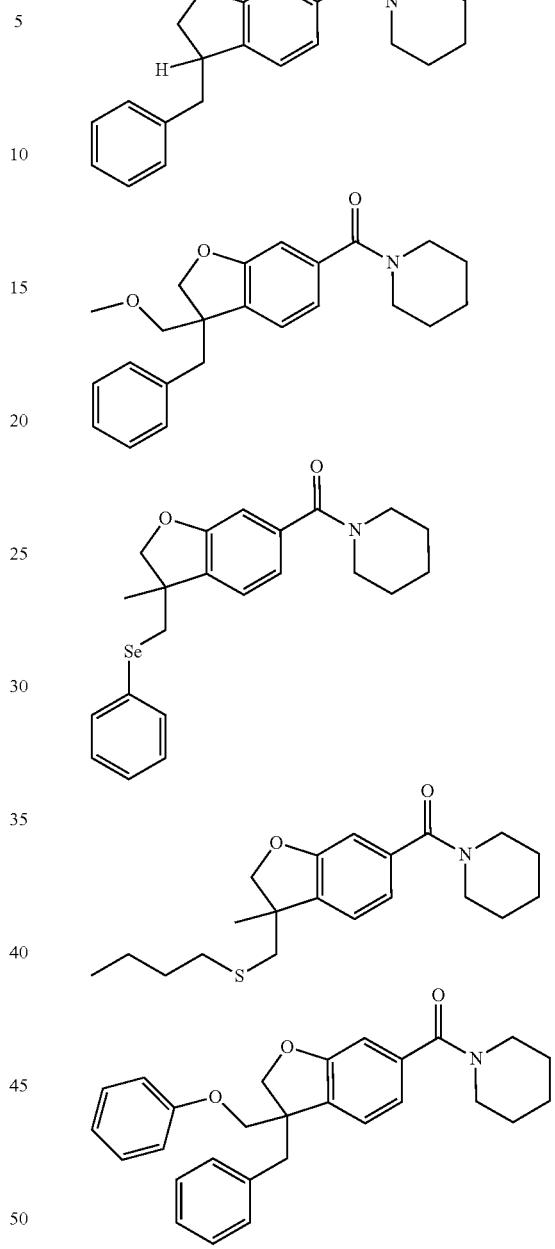

The present invention is illustrated by the following examples. It is to be understood that the particular examples, materials, amounts, and procedures are to be interpreted broadly in accordance with the scope and spirit of the invention as set forth herein.

EXAMPLES

Example 1: MDA7 SDD HPMCAS Formulation Data

The inventors carried out experiments to evaluate the ability of different pharmaceutical carriers to improve the bioavailability of 3-benzyl-3-methyl-2,3-dihydrobenzofuran-6-carboxylic acid-piperidine amide (MDA7).

Initial experiments with a wide variety of different lipid formulation systems, such as Campul, Kolliphor RH40, Peceol, polyethylene glycol rich surfactants, and glycerides. However, all of the lipid formulations tested showed poor bioavailability.

In the first round of testing, experiments were carried out using crystalline API, 25% MDA7: HPMCAS-H, 25% MDA7: Eudragit L100, 25/65/10%:HPMCAS-M:TPGS, 25/65/10% MDA7:PVP VA64:TPGS, and 40% MDA7: HPMCAS-M. The results of these experiments are shown in FIG. 1, and Table 1 below. Again, all of the SDD formulations showed an enhancement in free drug compared with crystalline API, while HPMCAS-H SDD provided the best sustainment of solubilized drug.

TABLE 1

MDA7 GB/IB Non-Sink Microcentrifuge Dissolution Test Results

| Sample | $C_{max90}$ (μg/mL) | $AUC_{90}$ (min*μg/mL) | $C_{90}$ (μg/mL) | $Ultra_{90}$ (μg/mL) | $C_{1200}$ (μg/mL) | $Ultra_{1200}$ (μg/mL) |
|---|---|---|---|---|---|---|
| Crystalline API | 31 | 2,360 | 31 | 31 | 31 | 31 |
| 25% MDA7: HPMCAS-H | 239 | 17,620 | 173 | 164 | 121 | 120 |
| 25% MDA7: Eudragit L100 | 237 | 10,170 | 103 | 69 | 66 | 61 |
| 25/65/10% MDA7: HPMCAS-M:TPGS | 330 | 13,920 | 114 | 112 | 90 | 91 |
| 25/65/10% MDA7: PVP VA64:TPGS | 245 | 11,910 | 107 | 105 | 94 | 85 |
| 40% MDA7: HPMCAS-M | 282 | 10,320 | 79 | 78 | 65 | 60 |

The inventors then carried out experiments to evaluate the microcentrifuge dissolution results for various concentrations of MDA7 encapsulated by a spray-dried dispersion (SDD) of various polymers. All of the SDD polymers showed an enhancement of drug solubilization compared to crystalline MDA7. In particular, formulations using hydroxypropyl methylcellulose acetate succinate (HPMCAS) showed better sustainment in comparison with other formulations.

Figure 2:
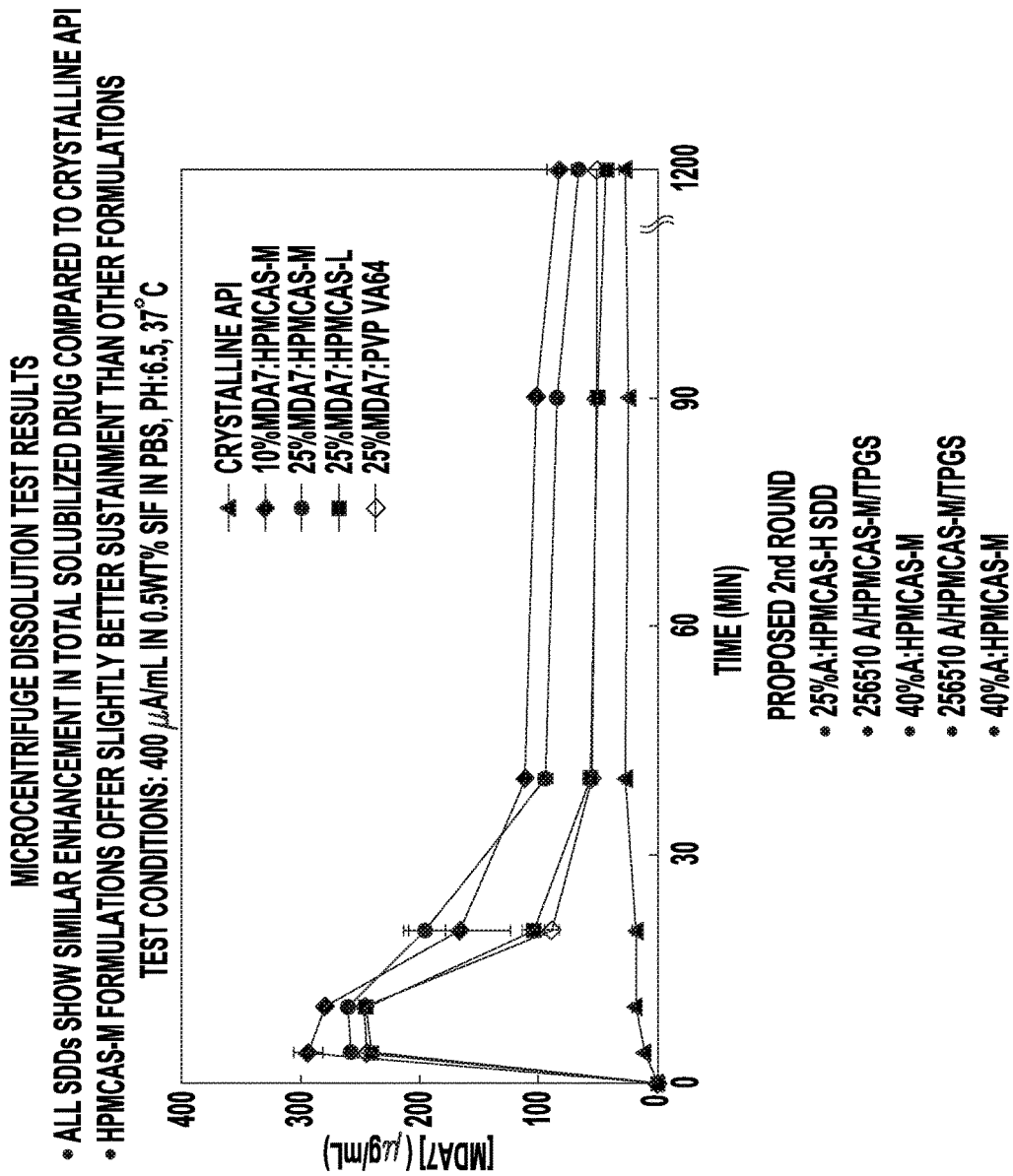
FIG. 2 provides a graph showing microcentrifuge dissolution test results, in which all SDDs show similar enhancement in total solubilized drug compared to crystalline API and HPCAS-M formulations offer slightly better sustainment than other formulations.

In the second round of testing, experiments were carried out using crystalline API (active pharmaceutical ingredient; MDA7), 10% MDA7 in HPMCAS-M SDD, 25% MDA7 in HPMCAS-M SDD, 25% MDA7 in HPMCAS-L SDD, and 25% MDA7:PVP VA64 SDD. The results of these experiments are shown in FIG. 2, and Table 2 below. The test conditions were 400 μgA/mL in 0.5 wt % SIF in PBS, pH 6.5, 37° C.

TABLE 2

Microcentrifuge Dissolution Test Results

| Sample | $C_{max90}$ (μg/mL) | $AUC_{90}$ (min*μg/mL) | $C_{90}$ (μg/mL) | $Ultra_{90}$ (μg/mL) | $C_{1200}$ (μg/mL) | $Ultra_{1200}$ (μg/mL) |
|---|---|---|---|---|---|---|
| Crystalline API | 27 | 2,010 | 24 | 20 | 28 | 24 |
| 10% MDA7: HPMCAS-M SDD | 294 | 12,630 | 102 | 100 | 82 | 78 |
| 25% MDA7: HPMCAS-M SDD | 260 | 11,690 | 84 | 73 | 67 | 53 |
| 25% MDA7: HPMCAS-L SDD | 245 | 7,910 | 50 | 41 | 43 | 32 |
| 25% MDA7: PVP VA64 SDD | 247 | 7,720 | 51 | 43 | 50 | 33 |

Example 2: Pharmacokinetics of Oral MDA7 Formulation Following Administration to Dogs The purpose of this study was to provide plasma samples to investigate the pharmacokinetics of MDA-007 following a single intravenous or oral gavage dose administration to male beagle dogs.

The test materials used in dosing for this study are shown in Table 3.

TABLE 3

Test Materials Used

| Date of Receipt | Test Material | Description | Amount Received | Storage Conditions |
|---|---|---|---|---|
| Received from Charles River Labs, Horsham, PA Oct. 19, 2015 | 20% Hydroxypropyl Beta Cyclodextrin (HPβCD) | Solution | 50 mL | 22 ± 5° C. |
| Received from Cleveland Clinic Oct. 19, 2015 | MDA-007 | White powder | 1 g | 22 ± 5° C./ Protect From Light |
| Received from Bend Research, Inc. Oct. 19, 2015 | 25% MDA-007:HPMCAS-H | White powder | 3.6 g | |
| | 25% MDA-007:HPMCAS-M | White powder | 3.7 g | |
| | 40% MDA-007:HPMCAS-M | White powder | 2.3 g | |

The dose formulations were initiated on the day of dosing by Test Facility personnel according to protocol specifications and Sponsor guidelines. Formulations for Session 1 (Groups 1 and 2) were prepared as follows:

For Group 1, 200.27 mg of compound MDA-007 was combined with 40.05 mL of 20% HPβCD. The mixture was vortexed then stirred at room temperature for 93 minutes forming a clear yellow solution at a concentration of 5 mg/mL for intravenous dosing. The intravenous dose solution was sterile-filtered using a Millex GV PVDF 0.22 μm filter (Millipore) prior to dosing.

Due to adverse clinical effects observed following dosing of Dog1001 and Dog1002, the formulation was modified. Using clean technique, an aliquot of the 5 mg/mL Group 1 formulation (2.8 mL) was combined with 20% HPβCD (4.2 mL), and vortexed to form a clear yellow solution at a concentration of 2 mg/mL for intravenous dosing.

For Group 2, 763.08 mg of compound MDA-007 was combined with 190.77 mL of 0.5% Hydroxypropyl methylcellulose (HPMC). The mixture was repeatedly vortexed and stirred for 80 minutes to produce a yellow homogeneous suspension at a target concentration of 4 mg/mL for oral dosing.

Formulations for Session 2 (Groups 3-5) were prepared as follows:

For Group 3, 1.5995 g of MDA-007 Formulation A (25% MDA-007:HPMCAS-H) was transferred to a mortar. The desired volume of 0.5% HPMC (99.97 mL) was added incrementally, while mixing the test article with a pestle, until a homogeneous suspension formed. The mixture was then transferred to a glass formulation bottle and stirred to produce a white homogeneous suspension at a target concentration of 4 mg/mL (adjusted for drug content) for oral dosing.

For Group 4, 1.6016 g of MDA-007 Formulation B (25% MDA-007:HPMCAS-M) was transferred to a mortar. The desired volume of 0.5% HPMC (100.1 mL) was added incrementally, while mixing the test article with a pestle, until a homogeneous suspension formed. The mixture was then transferred to a glass formulation bottle and stirred to produce a white homogeneous suspension at a target concentration of 4 mg/mL (adjusted for drug content) for oral dosing.

For Group 5, 1.0038 g of MDA-007 Formulation C (40% MDA-007:HPMCAS-M) was transferred to a mortar. The desired volume of 0.5% HPMC (100.38 mL) was added incrementally, while mixing the test article with a pestle, until a homogeneous suspension formed. The mixture was then transferred to a glass formulation bottle and stirred to produce a white homogeneous suspension at a target concentration of 4 mg/mL (adjusted for drug content) for oral dosing.

To ensure homogeneity, the oral dose formulations were stirred continuously on a magnetic stir plate until the completion of dosing. Upon completion of dosing, the residual dose formulations were discarded per proper procedure.

A total of fifteen male beagle dogs (plus one spare animal) were selected from the Test Facility's colony of non-naïve animals. The animals were assigned to the study based on acceptable health as determined by a Test Facility veterinarian following a pre-study health status check. The pre-study health status check included a physical exam, serum chemistry and hematology evaluations. The animals were placed into five groups of three animals per group. All animals were fasted overnight prior to dose administration. The final study design is presented in Table 4.

TABLE 4

Final Study Design

| Session | Group | No. of Males | Test Article | Active Dose Level (mg/kg) | As Is Conc. (mg/mL) | Active Dose Conc. (mg/mL) | Dose Volume (mL/kg) | Vehicle | Dose Route | Post-Dose Flush |
|---|---|---|---|---|---|---|---|---|---|---|
| 1 | 1A | 2 | MDA-007 | 5 | 5 | 5 | 1 | 20% HPβCD | IV | 3 mL Saline |
| | 1B | 1 | | 1 | 2 | 2 | 0.5 | | | |
| 2 | 3 | 3 | MDA-007 | 10 | 4 | 4 | 2.5 | 0.5% HPMC | PO | 20 mL water |

TABLE 4-continued

Final Study Design

| Session | Group | No. of Males | Test Article | Active Dose Level (mg/kg) | As Is Conc. (mg/mL) | Active Dose Conc. (mg/mL^) | Dose Volume (mL/kg) | Vehicle | Dose Route | Post-Dose Flush |
|---|---|---|---|---|---|---|---|---|---|---|
| 2 | 3 | 3 | MDA-007 (Formulation A) | 10 | 16 | 4 | 2.5 | 0.5% HPMC | PO | 20 mL water |
|   | 4 | 3 | MDA-007 (Formulation B) | 10 | 16 | 4 | 2.5 | 0.5% HPMC | PO | 20 mL water |
|   | 5 | 3 | MDA-007 (Formulation C) | 10 | 16 | 4 | 2.5 | 0.5% HPMC | PO | 20 mL water |

Each animal in Group 1 received the prepared test article as a 30-60 second intravenous injection by way of a temporary percutaneous catheter placed in a peripheral vein. Doses were administered at the target dose levels and dose volumes indicated in the table above. Immediately after each intravenous dose, the catheter was flushed with 3 mL of saline prior to removal. Each animal in Groups 2-5 received the prepared test article by oral gavage at a target dose level of 10 mg/kg and at a dose volume of 2.5 mL/kg. After each oral dose, the gavage tube was flushed with 20 mL of water prior to removal.

Dosing was performed on Session 1 and Session 2 as detailed in the study protocol and was completed without incident. Dose administration and body weight data are presented in Table 3. Following dosing and at each sample collection time point the animals were observed for any clinically relevant abnormalities and those observations are summarized in the table on the following page.

Whole blood samples (1 mL each, Na Heparin anticoagulant) were collected from a peripheral vessel not used for intravenous dosing. For Group 1, the whole blood samples were collected prior to dosing and at 5, 15, 30 minutes, 1, 2, 4, 6, 8, 12 and 24 hours following intravenous dosing. For Groups 2-5, the whole blood samples were collected prior to dosing and at 15, 30 minutes, 1, 2, 4, 6, 8, 12 and 24 hours following oral dosing. All blood samples were mixed by inversion and placed on wet ice immediately after collection and were centrifuged at 2 8° C. to isolate plasma. The resulting plasma was transferred to individual polypropylene tubes in a 96-well plate format and immediately placed on dry ice until storage at nominally −70° C. before transfer to the Test Facility's bioanalysis group for concentration analysis.

Figure 3:
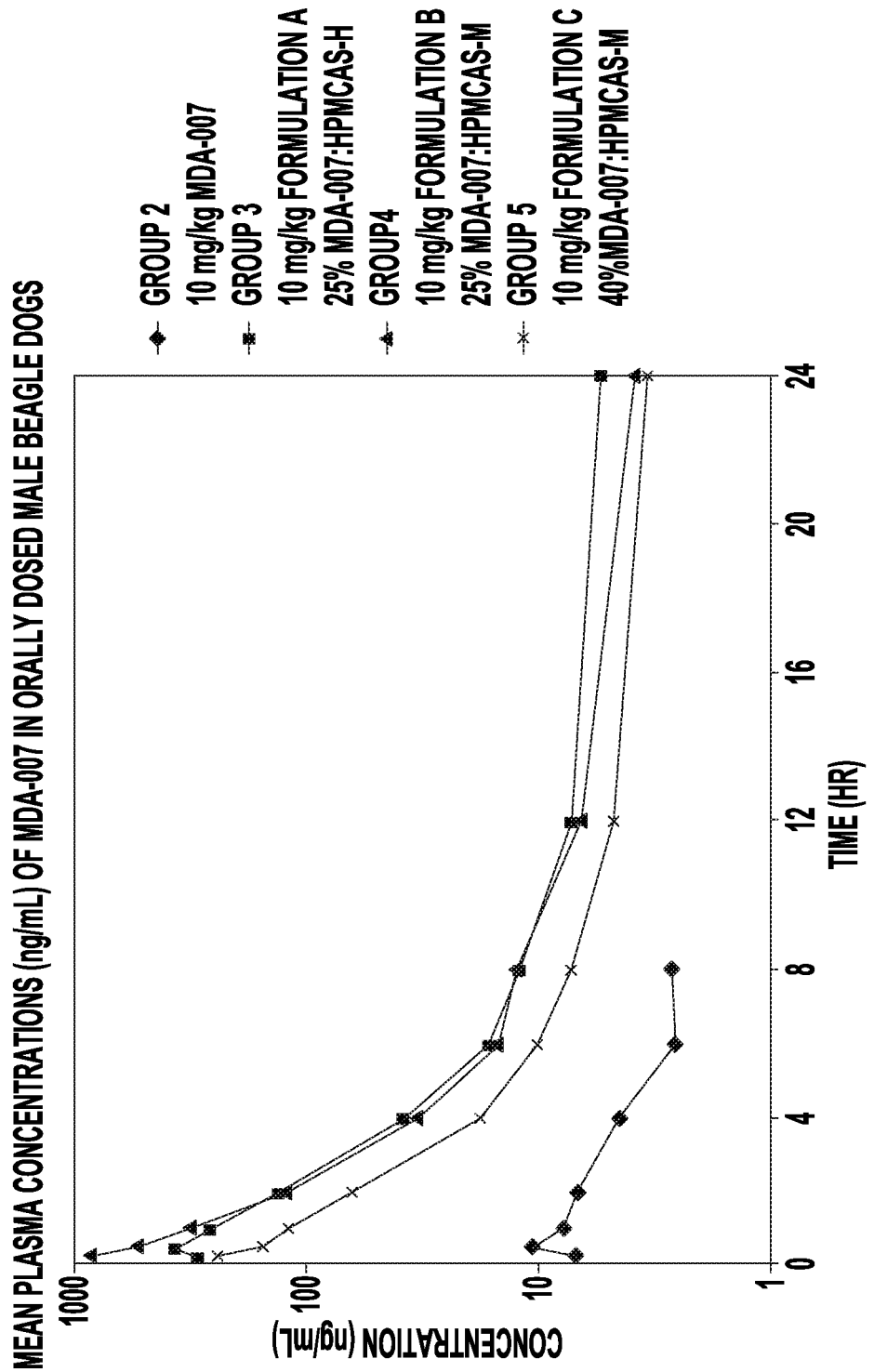
FIG. 3 provides a graph showing the pharmacokinetics of a test article following administration to male beagle dogs.

The plasma samples were analyzed for test article concentration using a Research Grade LC-MS/MS Assay. Bioanalytical data were forwarded to the Study Director for pharmacokinetic analysis. Pharmacokinetic parameters were estimated using Watson pharmacokinetic software (Thermo Electron Corporation, Version No. 7.2.0.02) employing a non-compartmental approach consistent with intravenous and extravascular routes of administration. Pharmacokinetic results are shown in FIG. 3.

Example 3: Dosing Suspension Stability and Physical and Chemical Stability of the Spray Dried Dispersion Summary 25% NTRX-07:HPMCAS-M SDD was selected as the lead formulation for this compound in a previous body of work based on in vitro and in vivo performance and predicted stability. HPMCAS-M=M grade hydroxypropyl methylcellulose acetate succinate; SDD=spray dried dispersion. Once a lead formulation was selected, experiments were conducted to select a suspension vehicle suitable for oral dosing, and establish a hold time for the suspension for toxicology studies. In preliminary suspension studies the dosing vehicle was identified as 0.5 wt % Methocel A4M/1.0 wt % Soluplus in pH 4 citrate buffer. These initial studies were expanded in this report to enable longer hold times and establish a suitable suspension concentration range for longer term toxicology studies. Results reported here show the suspensions can be held for up to 8 days, stirred at 2-8° C. with no impact to in vitro performance at suspension concentrations of 5-50 mgA/mL (mgA/mL=milligrams active per milliliter).

Physical and chemical stability studies of the SDD powder were also previously conducted and are reported here. These studies showed that at moderate storage conditions the SDD has acceptable chemical and physical stability. Some particle fusing was observed at elevated temperature, particularly with exposure to humidity. These fused particle led to slower dissolution and a lower $C_{max}$ (the maximum concentration of drug dissolved during dissolution testing) in dissolution testing. A small amount of chemical degradation was also observed in these samples. Based on these results it is recommended to store the SDD at 2-8° C. for long-term storage.

Suspension Stability

Suspensions were prepared at 5 mgA/mL and 50 mgA/mL in the previously identified vehicle, 0.5 wt % Methocel A4M/1.0 wt % Soluplus in pH 4 citrate buffer. The goal of this study was to establish suspension hold times over a concentration range to enable long-term toxicology studies. Suspensions were prepared and tested initially and at several timepoints up to 11 days for visual appearance, dissolution performance, and polarized light microscopy (PLM). Suspensions were stored with constant stirring at 5° C.

Visually, the initial suspensions were homogeneous, however, upon storage some separation was observed with a solid cake forming at the top, especially at the 50 mgA/mL concentration. This cake could be broken up and resuspended with some vigorous stirring. The dissolution results showed that the dosing accuracy was good through 8 days after thorough mixing. After 11 days the viscosity of the 50 mgA/mL suspension became limiting and dosing variability was observed as large error in the dissolution results.

Figure 4:
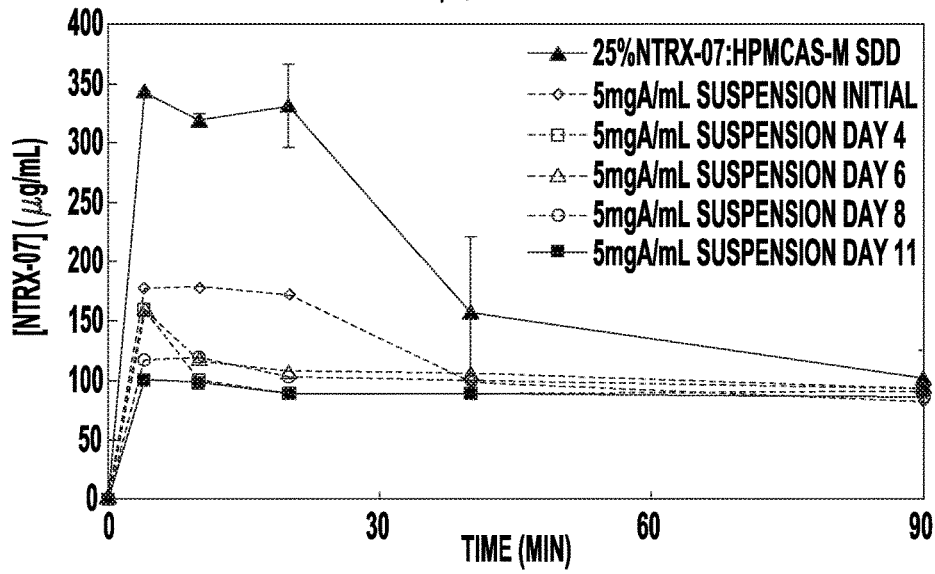
FIG. 4 provides a graph showing microcentrifuge dissolution performance of SDD in 5 mgA/mL suspension initially and after storage for up to 11 days at 5° C. compared to SDD powder.
Figure 5:
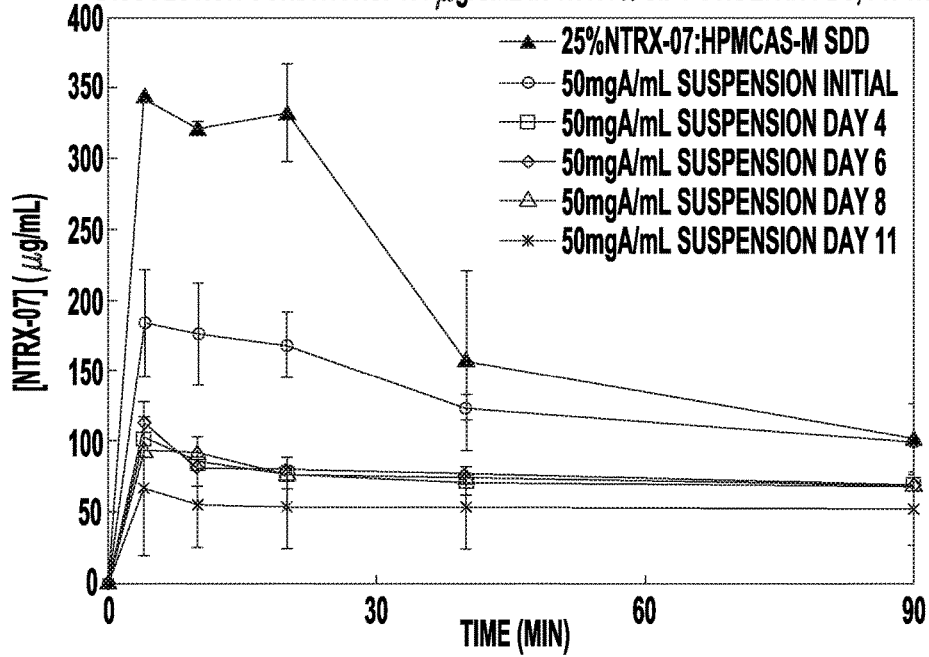
FIG. 5 provides a graph showing microcentrifuge dissolution performance of SDD in 50 mgA/mL suspension initially and after storage for up to 11 days at 5° C. compared to SDD powder.

Dissolution results for the suspension were similar at both concentrations through 11 days. The initial dissolution profile sustained longer than observed in previous suspension tests, the dissolution profiles on subsequent timepoints are more similar to what has been observed with suspension dosing previously on this project. Also, both concentrations have a slow drop in $C_{max}$ over time, however, the tests all drop to approximately 100 µgA/mL, which is similar to previous suspension results. The change in $C_{max}$ could be due to small agglomerates in the suspension which dissolve more slowly than SDD powder. At 11 days, the 50 mgA/mL suspension has large variability likely due to agglomeration leading to inconsistent dosing, therefore, a maximum hold time of 8 days is recommended. PLM images showed no evidence of crystals in either suspension through 11 days, therefore it is unlikely the drop in $C_{max}$ is due to the drug crystallizing. The dissolution data for the 5 mgA/mL and 50 mgA/mL suspensions are shown in FIG. 4 and FIG. 5 respectively, and corresponding Table 5 and Table 6.

TABLE 5

Microcentrifuge Dissolution Performance of SDD in 5 mgA/mL Suspension Initially and After Storage for Up to 11 Days at 5° C. Compared to SDD Powder.

| Sample | Cmax90 (µg/mL) | AUC90 (min*µg/mL) | C90 (µg/mL) | Ultra90 (µg/mL) |
|---|---|---|---|---|
| 25% NTRX-07:HPMCAS-M SDD | 343 | 17,320 | 103 | 98 |
| 5 mgA/mL Suspension Initial | 179 | 10,400 | 83 | 78 |
| 5 mgA/mL Suspension Day 4 | 160 | 8,190 | 87 | 79 |
| 5 mgA/mL Suspension Day 6 | 158 | 9,350 | 93 | 91 |
| 5 mgA/mL Suspension Day 8 | 119 | 8,880 | 93 | 95 |
| 5 mgA/mL Suspension Day 11 | 101 | 8,050 | 93 | 82 |

TABLE 6

Microcentrifuge Dissolution Performance of SDD in 50 mgA/mL Suspension Initially and After Storage for up to 11 Days at 5° C. Compared to SDD Powder.

| Sample | Cmax90 (µg/mL) | AUC90 (min*µg/mL) | C90 (µg/mL) | Ultra90 (µg/mL) |
|---|---|---|---|---|
| 25% NTRX-07:HPMCAS-M SDD | 343 | 17,320 | 103 | 98 |
| 5 mgA/mL Suspension Initial | 184 | 11,670 | 100 | 90 |
| 5 mgA/mL Suspension Day 4 | 104 | 6,580 | 70 | 70 |
| 5 mgA/mL Suspension Day 6 | 114 | 6890 | 70 | 70 |
| 5 mgA/mL Suspension Day 8 | 94 | 6,660 | 69 | 71 |
| 5 mgA/mL Suspension Day 11 | 68 | 4,770 | 52 | 54 |

SDD Physical and Chemical Stability

In this study, a 25% NTRX-07:HPMCAS-M SDD was set up on stability for 1, 3, and 6 months at 5° C. closed with desiccant, 25° C./60% RH open, and 40° C./75% RH open and closed with desiccant. The stability samples were prepared by placing ~150 mg SDD in HDPE bottles; closed conditions included a 1 g desiccant canister and HIS5 caps. The samples were analyzed for morphology by SEM, thermal characteristics by mDSC, performance by microcentrifuge dissolution, and assay and related substances for chemical stability. The results indicate the SDD is physically and chemically stable at moderate, room temperature conditions. Some particle fusing and degradation observed at elevated temperatures, therefore it is recommended to store the SDD at 5° C. in the absence of long term stability data.

Dissolution performance was evaluated over time by microcentrifuge dissolution in simulated intestinal media (0.5 wt % SIF powder in pH 6.5 PBS) at a dose of 500 mA/mL. Results show the results are unchanged at most conditions tested. Samples stored at 40° C./75% RH open condition show a drop in $C_{max}$ over time which may be due to slower dissolution due to fusing of the particles which was observed by SEM. Results indicated SDD is physically stable when protected from humidity. Dissolution profiles are shown in FIGS. 6A-6D.

SEM images were used to evaluate changes in morphology at various storage conditions. No changes were observed in samples stored at refrigerated or room temperature conditions. Slight fusing was observed after 6 months at 40° C./75% RH when protected from moisture and more significant fusing at this temperature when open to humidity. These results indicate good physical stability when kept at or below room temperature.

SDD was monitored over time by mDSC to look for physical changes such as phase separation or crystallization. The results so no change over time with a Tg similar to that of the initial, 62° C., at all storage conditions. No evidence of phase separation (i.e. a shifted Tg or the appearance of a second Tg) nor crystallization (i.e. a melt peak) were observed at any condition.

Finally, chemical stability was monitored over time by evaluating assay and related substances by HPLC. The results show almost no degradation at refrigerated and room temperature conditions. Some increase in the impurity at RRT 0.88 was observed at 40° C./75% RH. Degradation at this condition was faster in the sample not protected from humidity. The results indicate the SDD should have good chemical stability at refrigerated and room temperature conditions.

Conclusions

Based on the results reported in this memo it is recommended to prepare the dosing suspension at between 5 and 50 mgA/mL in 0.5 wt % Methocel A4M/1.0 wt % Soluplus in pH 4 Citrate buffer and use within 8 days after preparation. Suspension should be stored at 2-8° C. with stirring and mixed thoroughly before dosing each day.

The SDD powder should be stored for up to 6-months at room temperature or at 2-8° C. for long term storage. In order to ensure long term physical and chemical stability it is recommended to protect the SDD from humidity.

Methods

Suspension Stability

1. Prepare vehicle: 100 mM Citrate Buffer with 0.5 wt % Methocel A4M & 1 wt % Soluplus Vehicle
   a) Place 100 mL of deionized water into an Erlenmeyer flask.
   b) Add approximately 1.64 g of citric acid and 0.43 g Sodium Citrate, stir to dissolve.
   c) Once dissolved, heat solution to 80° C. with stirring.
   d) Accurately weigh and transfer approximately 0.5 g of Methocel A4M to the heated solution.
   e) Stir vigorously to suspend undissolved polymer.
   f) Transfer the Erlenmeyer flask of hot solution to an ice bath and continue stirring until polymers dissolve. (Approximately 15 minutes).
   g) Accurately weigh and transfer approximately 1.0 g of Soluplus to the cooled solution with stirring.
   h) Store solution at 5° C. for up to one month.
2. Prepare Suspension
   a) a. Place required mass of SDD into a mortar.
   b) b. Using a syringe, draw up required volume of the suspension vehicle.
   c) Connect a needle to the syringe before adding vehicle to mortar.
   d) Transfer suspension vehicle drop-wise into mortar with SDD and mix with pestle until a uniform suspension is made. Note: SDD does not wet easily; make sure to mix well with pestle after each drop of vehicle is added.

Once mixture is a homogeneous suspension in the mortar, more vehicle can be added in between mixing steps.
e) Repeat step d until the suspension vehicle has been added in entirety and is well mixed.
f) Transfer solution to an appropriately sized vial with a stir bar. Store at 5° C. with constant stirring. Note: Some phase separation was observed with solids collecting at the top of the vial; make sure these are we mixed thoroughly into the suspension prior to dosing to ensure a homogeneous suspension and accurate dosing.

Suspension was monitored for stability using the dissolution method included in this appendix. An appropriate volume of suspension was pipetted into each of two tubes to target the intended dissolution dose (i.e. to dose a 5 mgA/mL suspension at a dose of 400 mA/mL:

(0.4 mgA/mL$_{target\ dose}$*1.8 mL$_{total\ volume}$/(5 mgA/mL$_{suspension\ concentration}$)=0.14 mL suspension per tube The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A pharmaceutical composition comprising a pharmaceutically acceptable carrier suitable for oral administration and the compound

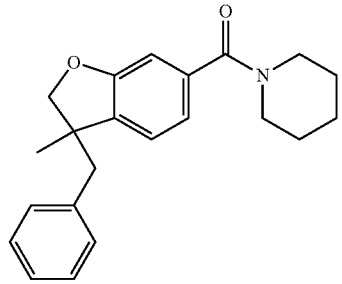 [SMILES: CC1(Cc2ccccc2)COc2cc(C(=O)N3CCCCC3)ccc21]

wherein the pharmaceutically acceptable carrier is a hydroxypropyl methylcellulose acetate succinate subtype M (HPMCAS-M) spray-dried dispersion, and wherein the compound is 25% (wt) of the pharmaceutical composition.

2. A method of treating neuropathic pain in a subject, said method comprising administering to the subject in need of such treatment, a therapeutically-effective amount of the pharmaceutical composition according to claim 1.

* * * * *